United States Patent [19]
Schäfer et al.

[11] Patent Number: 6,010,494
[45] Date of Patent: Jan. 4, 2000

[54] CONNECTION SYSTEM FOR MEDICAL APPLICATIONS

[75] Inventors: Dieter Schäfer, Rüsselsheim, Germany; Thomas Frei, Lützelflüh, Switzerland

[73] Assignee: Disetronic Licensing Ag, Switzerland

[21] Appl. No.: 09/048,681

[22] Filed: Mar. 26, 1998

[30] Foreign Application Priority Data

Mar. 26, 1997 [SE] Sweden ................................ 0730/97

[51] Int. Cl.[7] .......................... A61M 25/00; A61M 5/00
[52] U.S. Cl. .......................... 604/533; 604/536; 604/264
[58] Field of Search .................................. 604/177, 174, 604/179, 180, 283, 905, 272, 274, 264, 268, 201, 205, 239, 411, 280, 167, 533–536; 128/DIG. 26

[56] References Cited

U.S. PATENT DOCUMENTS

| | | | |
|---|---|---|---|
| 1,899,492 | 2/1933 | Beebe | 604/274 |
| 3,677,245 | 7/1972 | Welch | 604/283 |
| 4,475,548 | 10/1984 | Muto | 604/167 |
| 4,537,593 | 8/1985 | Alchas | 604/411 |
| 4,735,611 | 4/1988 | Anderson et al. | 604/130 |
| 5,104,389 | 4/1992 | Deem et al. | 604/264 |
| 5,247,942 | 9/1993 | Prather et al. | 604/283 |
| 5,324,270 | 6/1994 | Kayan et al. | 604/167 |
| 5,407,434 | 4/1995 | Gross | 604/167 |
| 5,429,609 | 7/1995 | Yoon | 604/167 |
| 5,460,616 | 10/1995 | Weinstein et al. | 604/167 |
| 5,464,397 | 11/1995 | Powers, Jr. | 604/283 |
| 5,466,230 | 11/1995 | Davila | 604/283 |
| 5,728,078 | 3/1998 | Powers, Jr. | 604/283 |
| 5,772,643 | 6/1998 | Howell et al. | 604/283 |
| 5,776,125 | 7/1998 | Dudar et al. | 604/411 |
| 5,782,817 | 7/1998 | Franzel et al. | 604/256 |
| 5,814,026 | 9/1998 | Yoon | 604/280 |

*Primary Examiner*—Wynn Wood Coggins
*Assistant Examiner*—Sharon Finkel
*Attorney, Agent, or Firm*—Dorsey & Whitney LLP

[57] ABSTRACT

The present invention provides a connection system for connecting a cannula to a device, the system involving a chamber operably coupled to the device, wherein the chamber has two apertures and contains a flexible substance, one of the apertures operably coupled to the device and both apertures operably linked by a channel defined in the flexible substance, the cannula having a cannula diameter and an end with a larger diameter than said cannula diameter.

16 Claims, 3 Drawing Sheets

CONNECTION SYSTEM FOR MEDICAL APPLICATIONS

PRIORITY CLAIM

This application claims priority of Swiss patent application 1997 0730/97, filed Mar. 26, 1997, which is hereby fully incorporated herein by reference.

BACKGROUND OF THE INVENTION

1. Field of the Invention

The present invention refers to a connection system for connecting a cannula with a rounded cannula end and a chamber containing a flexible substance and two apertures, the flexible substance connecting both apertures via a channel, wherein the rounded cannula end is made of an inorganic material.

2. Description of the Related Art

Various connection systems between a catheter and a body are known in medical engineering. Patent specification WO 89/06987 describes a connection system between a port system implantable inside the human body tissue and a catheter. A port chamber is arranged in a human or animal body to which a catheter remaining inside the body and an external catheter, pushed from the outside into the port chamber, can be attached. The inside of the port chamber contains a silicon membrane which can be punctured by the external catheter. A cannula is attached to the external catheter to avoid damaging the membrane during puncturing, withthe cannula end puncturing the silicon membrane containing a spherical end. Such a system is sold under the PERCUSEAL® trademark. The disadvantage of this system is that the spherical end molded on the cannula is made of plastic. The plastic surface contains brows, is extremely rough and damages the silicon membrane when the cannula is inserted into the port chamber. A damaged silicon membrane can no longer satisfactorily fulfill its function of preventing foreign bodies from entering the body.

Furthermore, connection systems between a cannula carrier for subcutaneous or intravenous steel or Teflon cannulas and a catheter are known. In many cases the steel or Teflon cannula supported by a carrier attached to the skin is releasably connected to a puncturing tool which assists in pushingthe canula under the skin or into a vien. After correctly positioning the cannula, the puncturing tool is removed and an infusion catheter with a cannula support is coupled in its place. For the coupling, a pointed coupling cannula attached to the infusion catheter is used which is pushed into a respective receiving element in the cannula carrier. The insertion of the pointed coupling cannula is often problematic as an incorrect insertion angle can cause the tip to penetrate the side wall instead of running inside the guided channel. The infusion catheter also has to be secured to the cannula carrier with a fixing device to prevent detachment of the coupling cannula from the cannula carrier. Such a coupling mechanism is, for instance, described in patent specification WO 94/20160.

Connection systems between drug ampoules and an infusion catheter are also known. In most cases, the infusion catheter contains a female Luer at the end facing the ampoule with the ampoule containing a male Luer. A connection is formed by pushing the female Luer over the male Luer. The disadvantage of this system is that the connection between the male and female Luer is highly tolerance-dependent and that already slight angular deviations can cause a leak.

SUMMARY OF THE INVENTION

The invention aims to remedy these disadvantages. The invention aims to provide a connection system for connecting a container containing a drug to a container or body receiving a drug, which can be used several times and permits certain manufacturing tolerances without adversely affecting the imperviousness of the system.

The invention also solves the task with a connection system for connecting a cannula with a rounded cannula end and a chamber containing a flexible substance and two apertures, the flexible substance connecting both apertures via a channel, wherein the rounded cannula end is made of an inorganic material.

The invention offers the principle advantages that due to the material selection and processing according to the invention the flexible membrane in a respective chamber is no longer damaged to the same extent as in a cannula with a molded plastic ball and that the flexibility of the membrane can compensate for certain manufacturing tolerances.

BRIEF DESCRIPTION OF THE DRAWINGS

Preferred embodiments of the invention are shown in the figures, in which.

DESCRIPTION OF THE PREFERRED EMBODIMENTS

Figure 1:
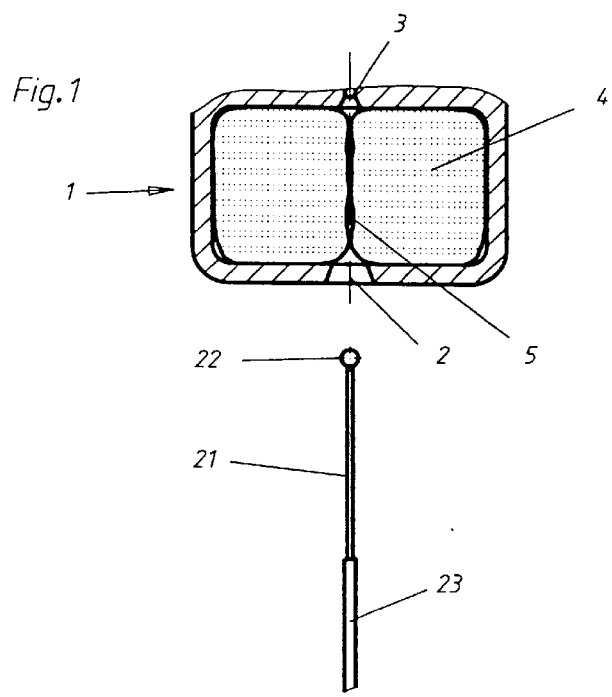
FIG. 1 represents a connection system according to the invention.

As shown in FIG. 1, a connection system according to the invention consists of a membrane chamber 1 with two opposing apertures 2, 3 of a different size, a membrane 4 arranged between the apertures 2, 3 made from a flexible material and containing in its center a connecting channel 5 between both apertures 2, 3 of the chamber 1. A cannula 21 with a spherical end 22 can be pushed through the facing aperture 2 of chamber 1 and through channel 5 to the opposing aperture 3 and can be removed again in the same manner. The diameter of the aperture 3 opposing the cannula 21 is smaller than the spherical end 22 of the cannula 1.

The membrane 4 in the chamber 1 is mechanically pressurized so that the channel 5 is self-closing and consequently prevents foreign bodies from penetrating into and through the channel 5. When inserting the cannula 21, the spherical end 22 must open the channel 5. The cannula is always surrounded by the membrane 4 so that when the spherical end 22 of the cannula 21 reaches the opposing aperture 3, sealing is guaranteed.

The chamber 1 and membrane 4 are designed in such a way that the spherical end 22 of the cannula 21 is retained in the opposing aperture 3 after its insertion. As the diameter of the opposite aperture 3 is smaller than the diameter of the spherical end 22 of the cannula 21, the cannula cannot be fully pushed through the chamber 1 but only up to the stop of the spherical cannula end 22 ate the internal chamber wall, level with the opposite aperture 3. The membrane 4 in the area of the opposite aperture 3 is formed in such a way that the spherical end 22 is pressed against the internal chamber wall of the opposing aperture 3.

Figure 2:
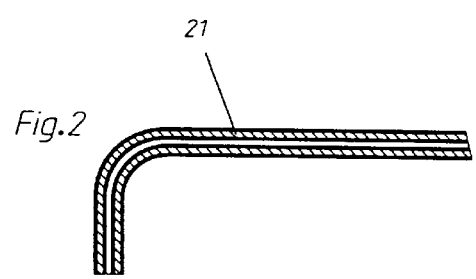
FIG. 2 represents a connection system according to the invention including a spherical end pushed over the cannula.
Figure 3:
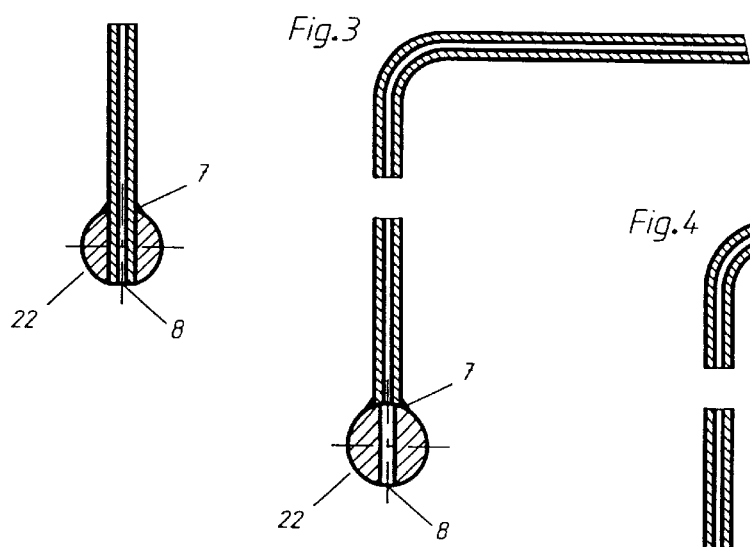
FIG. 3 represents a connection system according to the invention with a spherical end placed on the cannula.
Figure 4:
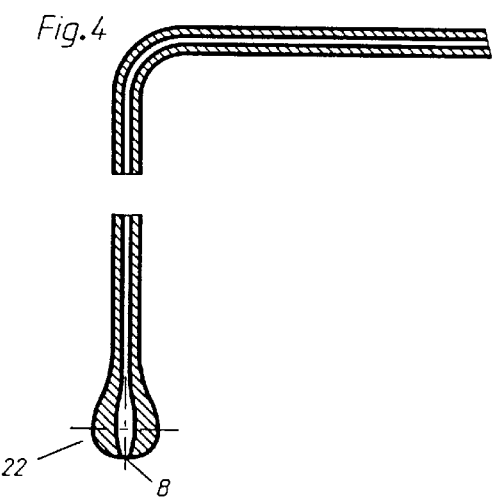
FIG. 4 represents a connection system according to the invention including a pressed cannula end.

In order to prevent damaging the membrane 4, the spherical cannula end 22 is preferably produced from an inorganic material and provided with a finely machined surface whose roughness does not exceed 0.8 μm. As shown in FIGS. 2–4, the spherical end containing a diametrical through-bore 8 can either be pushed over the cannula 21 (FIG. 2) or connected to the cannula (FIG. 3). It is also feasible to produce the cannula from a material which itself is rounded off by the pressure on the cannula end. In this case a spherical end is unlikely, which explains the respective design of FIG. 4.

The preferred material for the spherical end 22 or the rounded end 22 of the cannula 21 is chrome nickel steel.

The preferred material for the membrane 4 is silicon.

In case of placing or joining the spherical end 22 to the cannula 21, the unit is secured with a soldered join 7.

Figure 5:
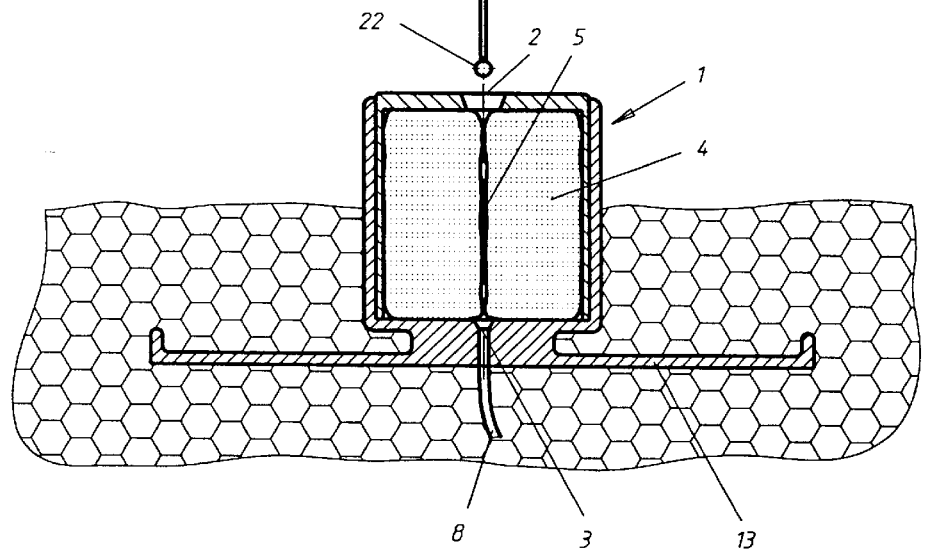
FIG. 5 represents a connection system according to the invention for a port system.

The connection system according to the invention has various types of application. FIG. 5 shows a port system which is inserted into the body of an organism. In this port system an anchoring plate 13, anchoring the membrane chamber 1 in the tissue, is directly connected to the membrane chamber 1.

The cannula 21 is pushed through the facing aperture 2 and then through the membrane chamber 5 up to the aperture 3 facing away from the cannula. Once the spherical cannula end 22 is located at the aperture 3 facing away from the cannula, the membrane 4 surrounds the spherical cannula end 22 in such a way that the cannula 21 is forced against the aperture 3 facing away from the cannula. An internal catheter 8 is directly connected to the aperture 3 facing away from the cannula so that a drug channel leading from an infusionhose 23 into the organism is created.

Instead of a connection to an infusion hose 23, the spherical end 22 of the cannula 21 can also be arranged on an injection device so that the injection device carries out an injection directly through chamber 1 into a body located behind the chamber.

Figure 6:
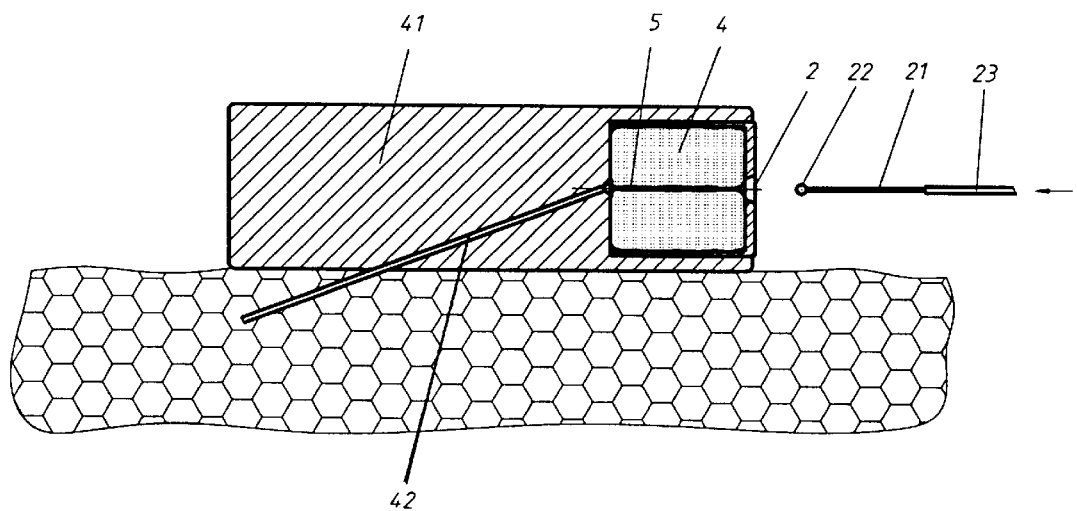
FIG. 6 represents a connection system according to the invention for subcutaneous or intravenous Teflon or steel cannula.

FIG. 6 shows a connection system according to the invention between a cannula carrier 41 for a subcutaneous Teflon cannula 42 and an infusion hose 23.

Figure 7:
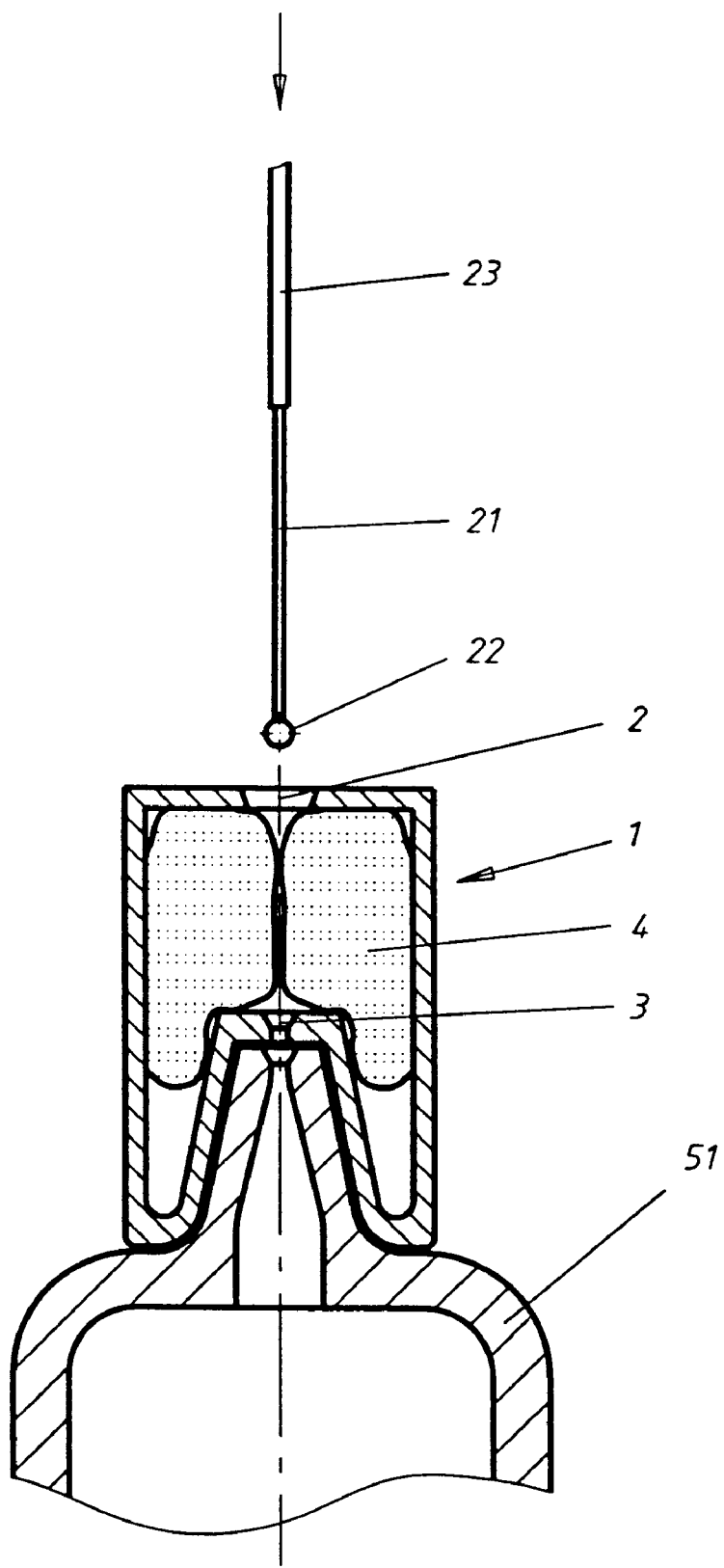
FIG. 7 represents a connection system according to the invention for a drug ampoule.

FIG. 7 shows a connection system according to the invention between an ampoule 51 and an infusion hose 23. The chamber 1 is attached to an ampulla 51. Via the connection system, drugs can be administered into the ampoule or the ampulla can be emptied.

We claim:

1. A connection system comprising a cannula with a rounded cannula end and a chamber having two apertures and containing a flexible substance, the flexible substance connecting both apertures via a channel, characterized in that the cannula is generally cylindrical and has a diameter and said rounded cannula end is made of an inorganic material and has a diameter larger than the diameter of the cannula.

2. The connection system according to claim 1, characterised in that the rounded cannula end is spherical.

3. The connection system according to claim 2, characterised in that the roughness of the cannula end does not exceed 0.8 μm.

4. The connection system according to claim 3, characterised in that the cannula end is made of metal.

5. The connection system according to claim 4, characterised in that the channel through the flexible substance is self-closing.

6. The connection system according to claim 5, characterised in that the chamber is also a port chamber.

7. A connection system for connecting a cannula to a device, said system comprising a chamber operably coupled to the device, said chamber having two apertures and containing a flexible substance, one of said apertures operably coupled to the device and said apertures operably linked by a channel defined in the flexible substance, said cannula having a cannula diameter and an end with a larger diameter than said cannula diameter.

8. The connection system according to claim 7, wherein the channel is self-closing.

9. The connection system according to claim 8, wherein the surface roughness of the spherical end does not exceed 0.8 μm.

10. The connection system according to claim 9, wherein the chamber is a link to one of a cannula support and an ampoule.

11. The connection system according to claim 9, wherein the chamber is a portion of an ampoule.

12. A method of coupling a cannula and another device, comprising the steps of:

providing a connection member having a wall defining a chamber, said chamber having two generally opposed apertures and containing a flexible material, one of said apertures operably coupled to the device, a channel defined in the flexible material and extending between said apertures; and providing the cannula with a generally spherical end having a larger diameter than the cannula, whereby said spherical end is receivable in the one of said apertures generally opposed to the one of said apertures operable coupled to the device and is movable through the channel to and from a position generally adjacent to the aperture operably coupled to the device.

13. A connection system for coupling an external substance delivery member and an internal catheter, said system comprising;

a connection member operably coupled to the catheter and having a wall defining a chamber, said chamber having two generally opposed apertures and containing a flexible material, one of said apertures operably coupled to the catheter, a channel defined in the flexible material and extending between said apertures; and wherein the external substance delivery member has a length and generally rounded end having a larger diameter than the length, whereby said generally rounded end is receivable in the one of said apertures generally opposed to the one of said apertures operably coupled to the catheter and is movable through the channel to and from a position generally adjacent to the aperture operably coupled to the catheter.

14. The connection system according to claim 13, wherein the rounded end is generally spherical.

15. The connection system according to claim 14, wherein the channel is self-closing.

16. The connection system according to claim 15, wherein the surface roughness of the generally spherical end does not exceed 0.8 μm.

* * * * *